United States Patent
Foreman et al.

(10) Patent No.: US 9,295,564 B2
(45) Date of Patent: Mar. 29, 2016

(54) FUSION METHODS USING AUTOLOGOUS STEM CELLS

(75) Inventors: Greg Foreman, Adrian, MI (US); Kevin Dunworth, Dripping Springs, TX (US); Robert J. Jones, Austin, TX (US)

(73) Assignee: SpineSmith Partners, L.P., Austin, TX (US)

( * ) Notice: Subject to any disclaimer, the term of this patent is extended or adjusted under 35 U.S.C. 154(b) by 1642 days.

(21) Appl. No.: 11/876,749

(22) Filed: Oct. 22, 2007

(65) Prior Publication Data

US 2009/0105825 A1 Apr. 23, 2009

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC ............. *A61F 2/4465* (2013.01); *A61F 2/4611* (2013.01); *A61F 2002/2835* (2013.01); *A61F 2002/3008* (2013.01); *A61F 2002/30678* (2013.01); *A61F 2002/30904* (2013.01); *A61F 2250/0098* (2013.01)

(58) Field of Classification Search
CPC ................ A61F 2/4455–2/447; A61F 2/4644; A61F 2/28; A61F 2002/4475; A61F 2002/4648; A61F 2002/2835; A61F 2002/2839
USPC ............................................ 623/17.11–17.16
See application file for complete search history.

(56) References Cited

U.S. PATENT DOCUMENTS

| | | |
|---|---|---|
| 4,309,488 A | 1/1982 | Heide et al. |
| 4,654,314 A | 3/1987 | Takagi et al. |
| 4,722,870 A | 2/1988 | White |
| 4,820,305 A | 4/1989 | Harms et al. |
| 4,950,296 A | 8/1990 | McIntyre |
| 4,955,908 A | 9/1990 | Frey et al. |
| 4,961,740 A | 10/1990 | Ray et al. |
| 5,015,247 A | 5/1991 | Michelson |
| 5,226,914 A | 7/1993 | Caplan et al. |
| 5,306,309 A | 4/1994 | Wagner et al. |
| 5,486,359 A | 1/1996 | Caplan et al. |
| 5,514,180 A | 5/1996 | Heggeness et al. |
| 5,702,449 A | 12/1997 | McKay |
| 5,728,159 A | 3/1998 | Stroever et al. |
| 5,755,798 A | 5/1998 | Papavero et al. |
| 5,766,253 A | 6/1998 | Brosnahan, III |
| 5,972,368 A | 10/1999 | McKay |
| 6,200,606 B1 | 3/2001 | Peterson et al. |
| 6,261,586 B1 | 7/2001 | McKay |
| 6,270,528 B1 | 8/2001 | McKay |
| 6,371,988 B1 | 4/2002 | Pafford et al. |
| 6,638,310 B2 | 10/2003 | Lin et al. |
| 6,706,067 B2 | 3/2004 | Shimp et al. |

(Continued)

FOREIGN PATENT DOCUMENTS

EP 0179695 3/1989

*Primary Examiner* — David Bates
*Assistant Examiner* — Olivia C. Chang
(74) *Attorney, Agent, or Firm* — Winstead PC

(57) ABSTRACT

A method and apparatus is provided for use in spinal fusion procedures. An exemplary interbody fusion device includes a synthetic non-metallic radiolucent interbody spacer having an opening formed between its top and bottom surfaces. A cancellous allograft plug is configured to be disposed within the opening formed in the spacer. The cancellous allograft plug can be reconstituted with a material that will help to facilitate fusion of the vertebrae.

12 Claims, 5 Drawing Sheets

(56) References Cited

U.S. PATENT DOCUMENTS

| | | |
|---|---|---|
| 6,761,739 B2 | 7/2004 | Shepard |
| 6,979,353 B2 * | 12/2005 | Bresina ................ 623/17.16 |
| 7,018,412 B2 | 3/2006 | Ferreira et al. |
| 7,018,416 B2 | 3/2006 | Hanson et al. |
| 7,048,765 B1 | 5/2006 | Grooms et al. |
| 7,204,851 B2 | 4/2007 | Trieu et al. |
| 7,595,043 B2 | 9/2009 | Hedrick et al. |
| 2002/0151976 A1 * | 10/2002 | Foley et al. ............. 623/17.11 |
| 2003/0093153 A1 | 5/2003 | Banick et al. |
| 2003/0139813 A1 * | 7/2003 | Messerli et al. .......... 623/17.11 |
| 2003/0171810 A1 | 9/2003 | Steiner |
| 2004/0078078 A1 | 4/2004 | Shepard |
| 2004/0082999 A1 | 4/2004 | Mathys et al. |
| 2004/0102850 A1 * | 5/2004 | Shepard ................ 623/17.16 |
| 2004/0122518 A1 | 6/2004 | Rhoda |
| 2004/0127990 A1 * | 7/2004 | Bartish et al. ............ 623/17.11 |
| 2005/0143822 A1 | 6/2005 | Paul |
| 2005/0169893 A1 * | 8/2005 | Koblish et al. ............. 424/93.7 |
| 2006/0106460 A1 * | 5/2006 | Messerli et al. .......... 623/17.11 |
| 2006/0200166 A1 | 9/2006 | Hanson et al. |
| 2006/0217807 A1 * | 9/2006 | Peterman et al. ......... 623/17.11 |
| 2008/0033572 A1 * | 2/2008 | D'Antonio et al. ........ 623/23.51 |
| 2008/0300634 A1 * | 12/2008 | Gray ....................... 606/280 |
| 2009/0105824 A1 | 4/2009 | Jones et al. |

\* cited by examiner

FUSION METHODS USING AUTOLOGOUS STEM CELLS

FIELD OF THE INVENTION

This invention relates to the field of spinal fusion. In particular, this invention is drawn to spinal fusion using autologous stem cells.

BACKGROUND OF THE INVENTION

The spine can be considered to be a series of movable segments made up of vertebrae and discs. Due to trauma, disease, and/or aging, the spine may be subject to degeneration. This degeneration may destabilize the spine and cause pain and/or nerve damage. Medical procedures are often required to either ease back pain, repair damage, or to prevent future damage.

One procedure that is often used to treat back pain or spinal damage is spinal fusion. Spinal fusion is a surgical technique used to combine two or more adjacent vertebrae. Supplemental bone tissue is used in conjunction with the patient's natural osteoblastic processes in a spinal fusion procedure. Spinal fusion is used primarily to eliminate back pain caused by the motion of the damaged vertebrae by immobilizing adjacent vertebrae. Conditions for which spinal fusion might be done include degenerative disc disease, treatment of a spinal tumor, a vertebral fracture, scoliosis, degeneration of the disc, spondylolisthesis, or any other condition that causes instability of the spine.

There is a need for spinal fusion devices and related spinal fusion procedures that adequately treats degenerative disc disease and other spinal conditions, while providing improvements over the prior art.

SUMMARY OF THE INVENTION

A method is provided for fusing adjacent vertebrae including providing a vertebral spacer, reconstituting a cancellous allograft plug using autologous stem cells, inserting a reconstituted cancellous allograft plug into an opening of the vertebral spacer, and inserting the vertebral spacer and reconstituted cancellous allograft plug between two adjacent vertebrae to facilitate the fusion of the two adjacent vertebrae.

Another embodiment of the invention provides a method of fusing adjacent vertebrae including isolating adult stem cells from a first person, providing a vertebral spacer, reconstituting a cancellous allograft plug using the isolated adult stem cells from the first person, inserting the reconstituted cancellous allograft plug into an opening of the vertebral spacer, and inserting the vertebral spacer and reconstituted cancellous allograft plug between two adjacent vertebrae of the first person to facilitate the fusion of the two adjacent vertebrae.

Another embodiment of the invention provides a method of fusing boney tissue including isolating adult stem cells from a first person, providing an implant device configured to facilitate the fusion of boney tissue, reconstituting carrier material using the isolated adult stem cells from the first person, using the reconstituted carrier material with the implant device, and installing the implant device and reconstituted carrier material in the proximity of the boney tissue to facilitate the fusion of the boney tissue.

Another embodiment of the invention provides a method of fusing adjacent boney tissue including providing an implant, configuring a carrier material to fit at least partially within an opening of the implant, reconstituting the carrier material using autologous stem cells, inserting the reconstituted carrier material into the opening of the implant, and inserting the implant and reconstituted carrier material between adjacent boney tissue to facilitate the fusion of the boney tissue.

Other features and advantages of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements and in which.

DETAILED DESCRIPTION

The present invention relates to spinal fusion implants and related spinal fusion procedures for use in cervical and lumbar applications. One type of spinal fusion is interbody fusion. Typically, an interbody fusion procedure places a bone graft between two adjacent vertebra in the area normally occupied by an intervertebral disc. In preparation for a spinal fusion procedure, the intervertebral disc is removed. A device may be placed between the vertebra to maintain spine alignment and disc height. Fusion then occurs between the endplates of the vertebrae. The present invention provides an interbody fusion device and related methods that provide various advantages over the prior art.

Generally, the present invention provides an interbody fusion device that may be used for cervical and lumbar interbody fusion. In one example, a first piece of the interbody fusion device is a load bearing device having an opening formed between its top and bottom surfaces. The first piece is designed to bear the axial loading from the end plates of adjacent vertebrae. A second piece of the interbody fusion device is a cancellous allograft plug configured to fit within the opening formed in the first piece. The cancellous allograft plug can be reconstituted with a material that will help to facilitate fusion of the vertebrae.

Figure 1:
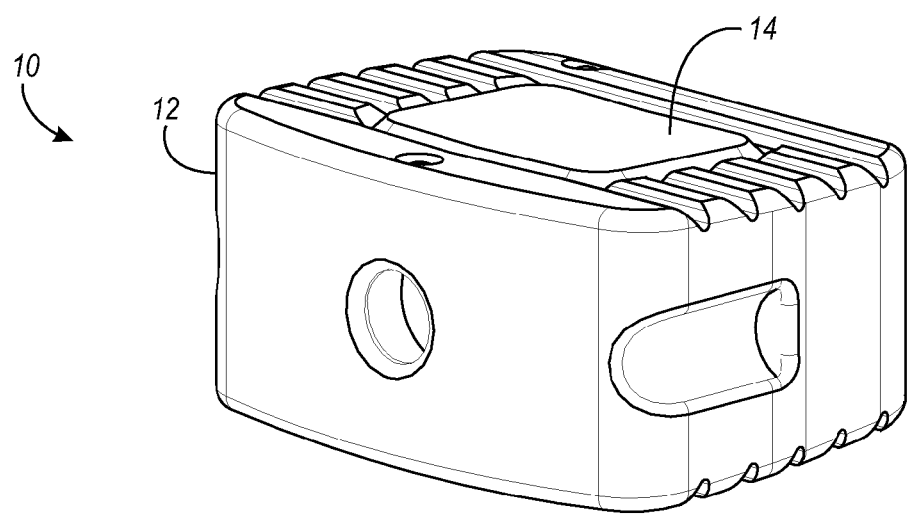
FIG. 1 is an isometric view of one example of an interbody fusion device of the present invention.

FIG. 1 is an isometric view of one example of an interbody fusion device of the present invention. FIG. 1 shows an interbody fusion device 10. The interbody fusion device 10 includes a load bearing interbody spacer 12 and a cancellous allograft plug 14, each of which are described in more detail below.

Figure 2:
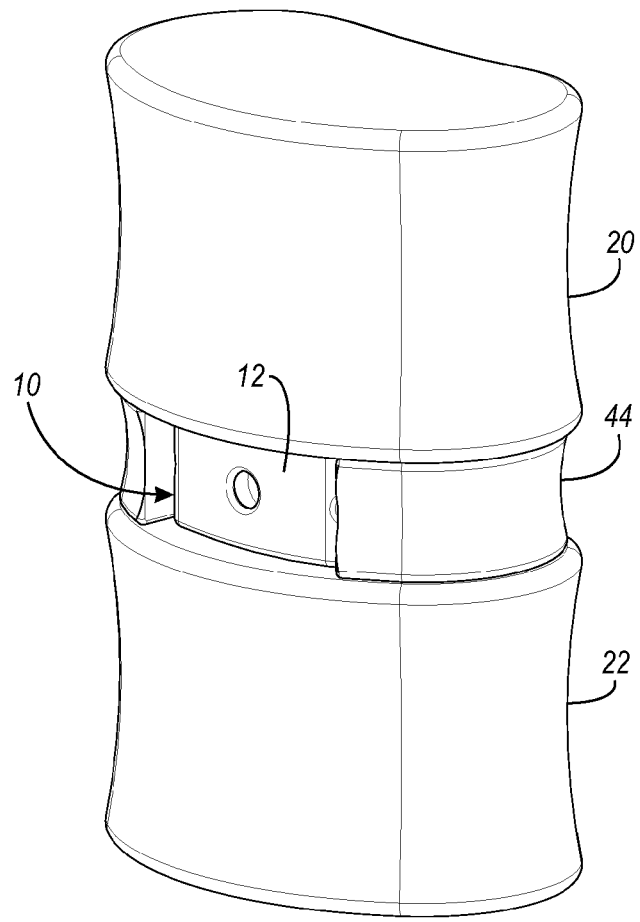
FIG. 2 is an isometric diagram of the interbody fusion device shown in FIG. 1 installed between the end plates of two adjacent vertebrae.

FIG. 2 is an isometric diagram of the interbody fusion device 10 shown in FIG. 1 installed between the end plates of two adjacent vertebrae 20 and 22 to facilitate the fusion of the vertebrae 20 and 22. The interbody fusion device 10 provides load bearing support as well as the proper spacing between the vertebrae 20 and 22 while fusion of the vertebrae takes place. As described in more detail below, the interbody fusion device 10 is positioned between the end plates of the vertebrae 20 and 22 within the vertebral body in the area usually occupied by the intervertebral disc.

Figure 3:
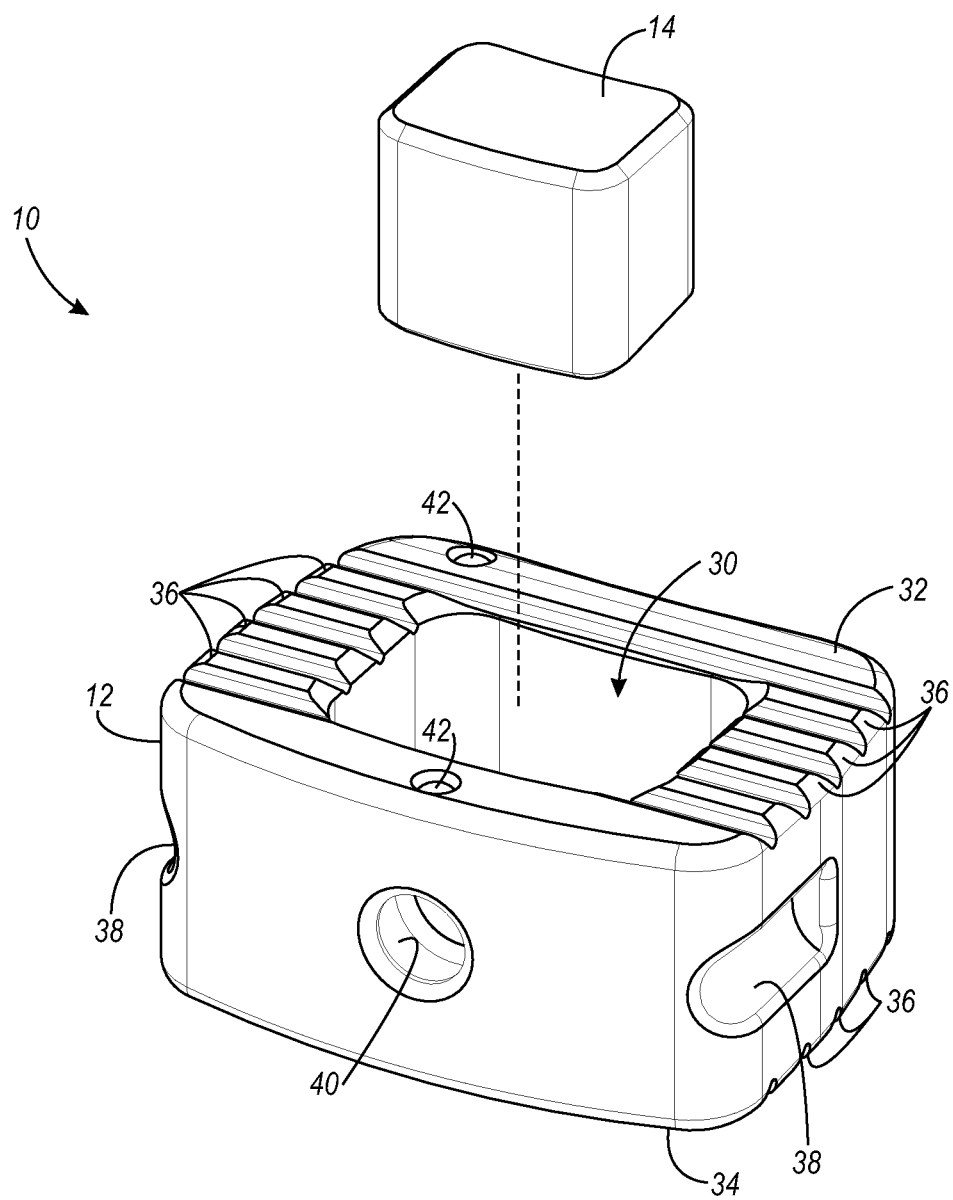
FIG. 3 is an exploded view of the interbody fusion device shown in FIG. 1.

FIGS. 3-6 are views illustrating various details of one example of an interbody fusion device of the present invention. FIG. 3 is an exploded view of the interbody fusion device 10, showing the load bearing spacer 12 and the cancellous allograft plug 14 separately. The interbody fusion device 10 is shaped to fit between adjacent vertebrae in the location of the intervertebral disc. The spacer 12 has an opening 30 formed between the upper and lower surfaces 32 and 34 of the spacer 12. The opening 30 allows the allograft plug 14 to be inserted into the spacer 12, as is described in detail below.

The spacer 12 also includes a plurality of ridges 36 formed on the top and bottom surfaces 32 and 34 of the spacer 12. The ridges 36 are angled and come to a point in such a way that the ridges 36 help to hold the spacer 12 to the end plates of the vertebrae to reduce the chance of anterior migration of the implant.

If desired, one or more openings can be formed in the spacer 12 to facilitate instrumentation devices. In the example shown in FIG. 3, two lateral scallops 38 are formed on opposite sides of the load bearing device 12. A central scallop 40 is formed on the front surface of the spacer 12. The two lateral scallops 38 facilitate gripping the fusion device 10 using a bi-fed instrument grip (not shown), such as a Kerrison-style implant holder or a forceps style implant holder. The central scallop 40 facilitates manipulation of the fusion device 10 using an implant pusher (not shown). An implant pusher would typically have a dimple formed that matches the central scallop 40 to prevent slippage of the implant pusher. The lateral and central scallops 38 and 40 allow all degrees of manipulation, while not compromising superior or inferior endplate interference.

In one example, a plurality of radio opaque markers 42 (two are shown in FIG. 3, others are shown in the figures described below) are embedded into the spacer 12. In some examples, the spacer 12 is made from a radiolucent material, which allows doctors to view the nearby vertebral bodies using X-rays without the spacer 12 blocking the view of the vertebral bodies. Since the spacer 12 is made from a radiolucent material, it may be difficult for a doctor to observe the fusion device during, or after a surgery. However, the radio opaque markers 42 will show up in an X-ray. Since the positions of the markers 42 are known relative to the spacer 12, a doctor can determine the position of the fusion device 10 in an X-ray by viewing the positions of the markers 42.

Figure 4:
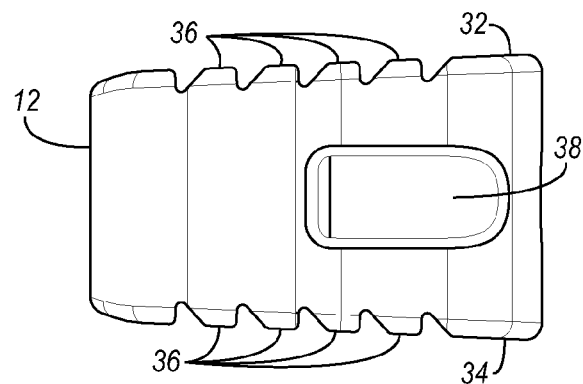
FIG. 4 is a side view of an interbody spacer.
Figure 5:
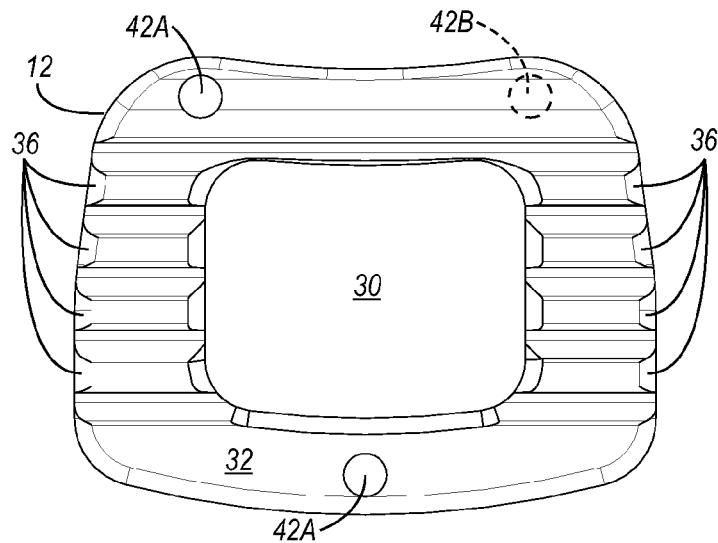
FIG. 5 is a top view of an interbody spacer.
Figure 6:
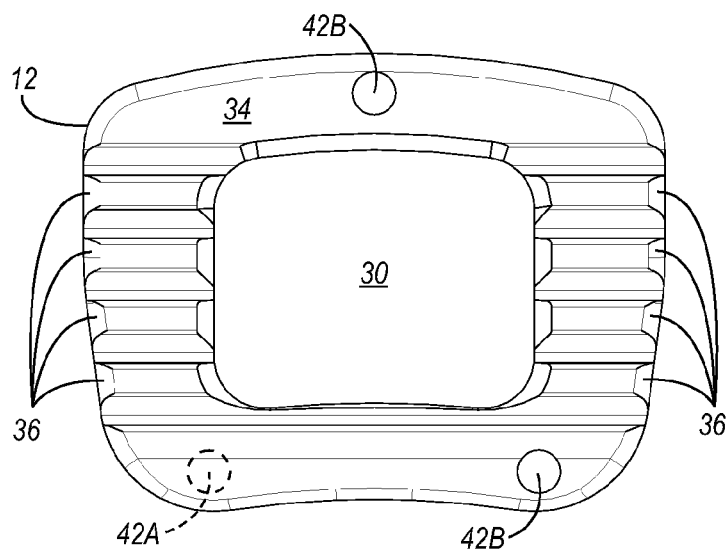
FIG. 6 is a bottom view of an interbody spacer.

FIG. 4 is a side view of the spacer 12. FIG. 4 shows a plurality of ridges 36 formed on the upper and lower surfaces 32 and 34 of the spacer 12. FIG. 4 also shows one of the lateral scallops 38 formed on the side of the spacer. FIG. 5 shows a top view of the spacer 12. As shown, a plurality of ridges 36 are formed in the upper surface 32 of the spacer 12. FIG. 6 shows a bottom view of the spacer 12. As shown, a plurality of ridges 36 are formed in the lower surface 34 of the spacer 12.

FIGS. 5 and 6 also show an exemplary size and shape of the opening 30. The opening 30 provides a relatively large graft volume, compared to a typical device. Prior to insertion between two vertebrae, the opening 30 can be filled with the cancellous alograft plug 14. As mentioned, the plug 14 can be reconstituted using a prepared material that will help to facilitate fusion of the vertebrae. Examples of a material include bone marrow, bone morphonogenic protein (BMP), Autologous Stem Cells, etc., to facilitate fusion through the opening 30.

FIGS. 5 and 6 also show an exemplary locations for a plurality of radio opaque markers 42. In the example shown, four markers 42 are embedded into the spacer 12, with two markers being disposed at or near each of the upper and lower surfaces 32 and 34. In FIGS. 5 and 6, the markers disposed at or near the upper surface 32 correspond to reference numeral 42A and the markers disposed at or near the lower surface 34 correspond to reference numeral 42B.

Figure 7:
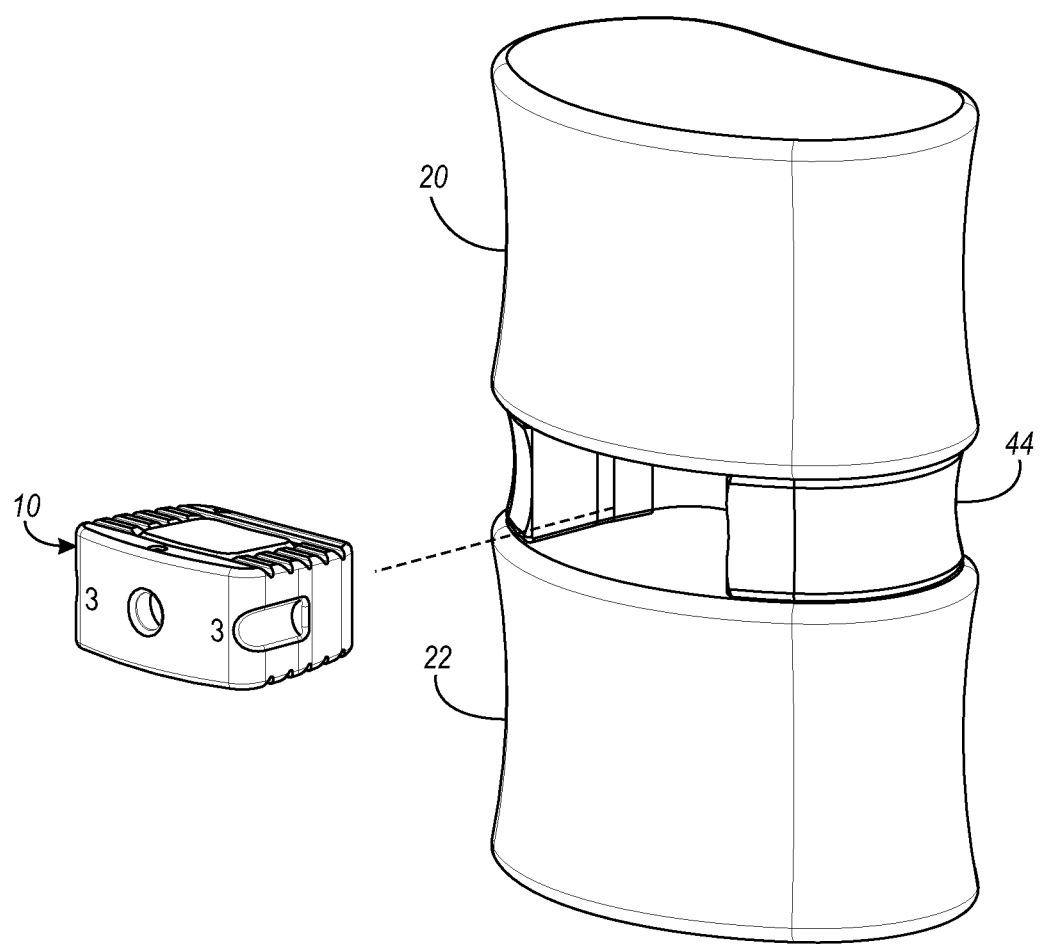
FIG. 7 is an exploded isometric diagram illustrating an interbody fusion device before being inserted between two vertebrae.

As described above, FIG. 1 is an isometric diagram of the interbody fusion device 10 with the cancellous allograft plug 14 inserted into the opening 30 formed in the spacer 12. The resulting assembly provides a load bearing structure that also allows desirable fusion of the adjacent vertebrae. Once the cancellous allograft plug 14 is reconstituted (described below) and inserted into the opening 30 of the spacer 12, the interbody fusion device can be inserted between adjacent vertebrae. Prior to the insertion of the interbody fusion device 10, the intervertebral disc is removed, so the interbody fusion device 10 can be placed between the vertebrae 20 and 22. In one example, a window is cut in the disc annulus 44. Next, portions of the nucleus pulposus are removed so that the interbody fusion device 10 can fit between the vertebrae 20 and 22 as shown in the figures. FIG. 7 is an exploded isometric diagram illustrating the interbody fusion device 10 after the plug 14 is inserted into the spacer 12 (FIG. 1), but before it is inserted between two vertebrae 20 and 22. FIG. 2 (described above) illustrates the interbody fusion device after it has been inserted between the vertebrae 20 and 22.

As mentioned, prior to insertion into the spacer 12, the cancellous allograft plug 14 is reconstituted, using a material that will help to facilitate fusion of the vertebrae. The reconstitution of the cancellous allograft plug can be accomplished using any desired technique, such as soaking the plug in the material. The reconstitution process makes the plug (or alternate carrier material) goes from a dehydrated or semi dehydrated state to a state where it is able to take on fluid and increase in mass and volume. Any desired material may be used, including bone marrow, bone morphonogenic protein (BMP), Autologous Stem Cells, etc. Note that, many materials from the body (e.g., blood, adipose tissue, muscle, organs, placenta, bone, teeth, bodily fluids, bone marrow, etc.) contain stem cells. When referring to autologous stem cells above, it is intended that autologous stem cells refers to stem cells that have been concentrated from the body.

One advantage of the present invention relates to the simplification of a spinal fusion surgery. Since the cancellous allograft plugs are pre-formed to fit into the openings of spacers (having known dimensions), the spacers and allograft plugs can be packaged or organized together prior to surgery. In other words, once a surgeon has selected a desired spacer, he or she will not have to make an effort and take time to select a plug, or to prepare custom fusion material. In one example, a spacer and a matching allograft plug are packaged together, making the surgical procedure easier. If desired, a single package can include one spacer and one plug, or a plurality of spacers and plurality of plugs. In another example, the spacers and plugs are packaged separately, with the spacers and plugs being appropriately labeled to allow a user to easily match the appropriate spacers and plugs.

When a surgeon prepares the vertebral body for the implant (e.g., by removing the disc and cleaning out the space between the vertebrae, etc.), the surgeon can determine what size and angle implant is desired. In one example, the spacers can be provided in several different predetermined heights. The plugs are each configured to be used with specific spacers. Therefore, a surgeon only need to determine the proper sized spacer to use, since each spacer corresponds to certain plugs. In one example, each type of spacers has an identifier (e.g., numbers and/or letters) on it. The identifier will tell a surgeon which plug to use with that particular spacer. FIG. 7 shows an example of how an identifier can be used. As shown, the spacer 12 in FIG. 7 has an identifier of "3." Presumably, a surgeon selected a "3" spacer based on a desired implant height, angle, etc. Once a "3" spacer is selected, a corresponding proper plug will be known, without the surgeon having to make a separate determination.

The spinal fusion device of the present invention can be made from any desired materials. In one example, the spacer is made from a synthetic non-metallic radiolucent material. A radiolucent material will allow a doctor to adequately view x-rays of bones without the spacer obstructing the view. As mentioned above, one or more radio opaque markers can be embedded into the spacer to allow a doctor to view the relative position of the spacers. Examples of synthetic non-metallic radiolucent material include, but are not limited to, thermoplastic materials such as Polyetheretherketones PEEK or Polyetherketoneketone (PEKK), carbon fiber, etc. The plug can also be made from any desired carrier material. Examples of carrier material include, but are not limited to, cancellous bone, cancellous chips, Hydroxylapatite, Helos, Tricalcium phosphate (bone ash), Collagen Sponge, etc.

As described above, the cancellous allograft plug can be reconstituted using autologous stem cells (i.e., adult stem cells, somatic stem cell, etc.) isolated from a patient's body. The autologous stem cells can be isolated/concentrated/grown/etc. from the patient's tissue using any desired method, as one skilled in the art would understand.

Figure 8:
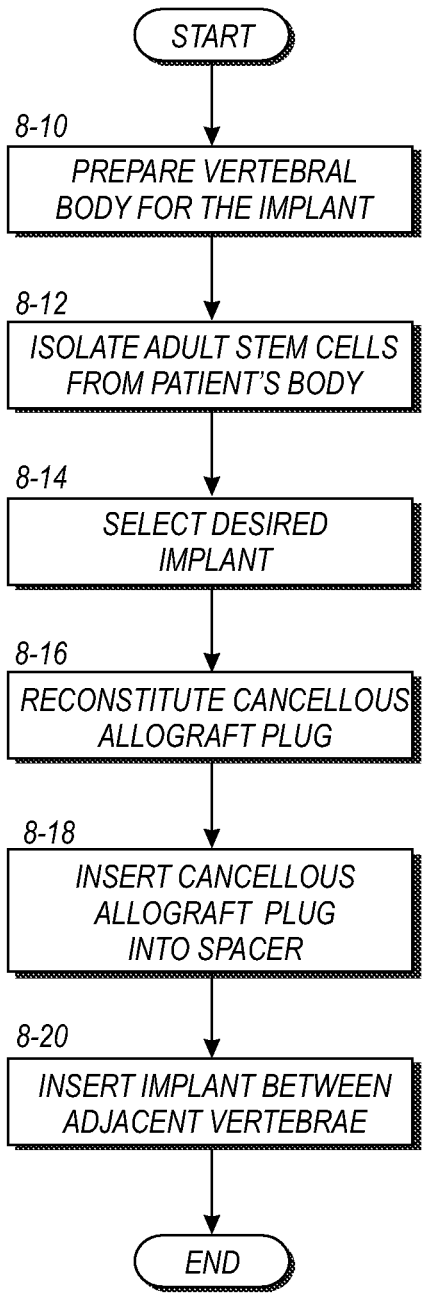
FIG. 8 is a flowchart illustrating one example of a spinal fusion procedure.

FIG. 8 is a flowchart illustrating an example of how an interbody fusion device of the present invention may be used in a spinal fusion procedure. At step 8-10, the vertebral body is prepared for the implant. For example, a window is cut in the side of the disc annulus (e.g., FIG. 7) to allow an interbody fusion implant to be inserted. The nucleus pulposus can also be cleaned out to provide room for the implant. In addition, a surgeon may scrape each vertebral body to help the fusion process. At step 8-12, adult stem cells are isolated from the patient's body. Adult stem cells may be isolated using any desired method for isolating/concentrating/growing/etc. adult stem cells. At step 8-14 a desired implant is selected. This selection can be based on factors such as the desired height between the adjacent vertebrae, the desired lordosis, etc. At step 8-16, the cancellous allograft plug is reconstituted, using the adult stem cells isolated from the patent in step 8-12. Once the allograft plug is ready, it can be inserted into the opening of the spacer (step 8-18) (FIG. 1). In another example, the plug can first be inserted into the spacer, and then reconstituted while it is inserted into the spacer. At step 8-20, the implant is inserted between the adjacent vertebrae using the appropriate instrumentation, as desired (FIGS. 7 and 2).

Figure 9:
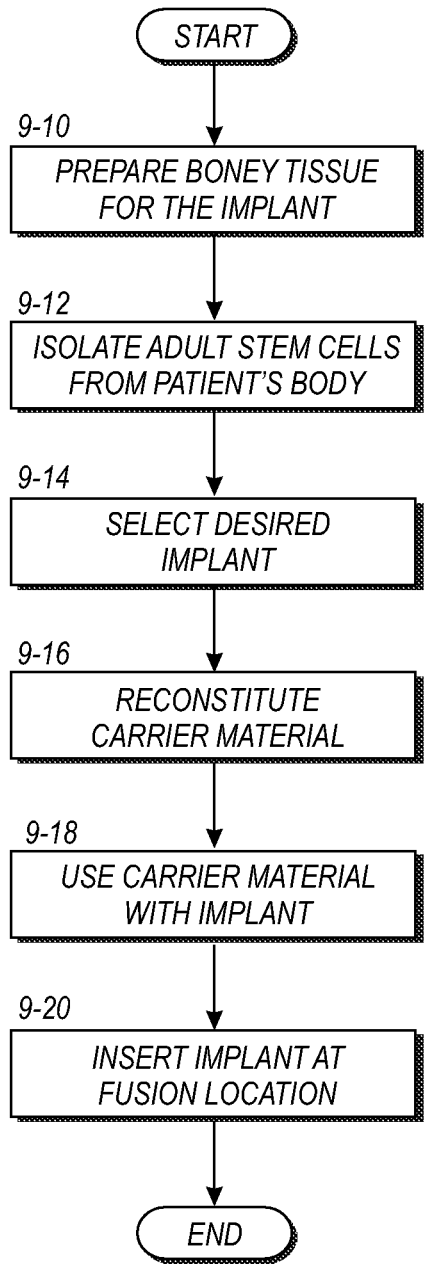
FIG. 9 is a flowchart illustrating one example of a boney tissue fusion procedure.

The present invention may also be used in other applications (both spinal applications and non-spinal applications). For example, for any application where it is desired to fuse boney tissue (e.g., broken bones, reconstructive surgeries, etc.), the present invention may be used. FIG. 9 is a flow chart illustrating an example of how an implant of the present invention may be used in a boney tissue fusion procedure.

At step 9-10, the boney tissue is prepared for the implant. This may involve things such as shaping the boney tissue to receive the implant, scraping the boney tissue, etc. At step 9-12, adult stem cells are isolated from the patient's body. Adult stem cells may be isolated using any desired method for isolating/concentrating/growing/etc. adult stem cells. At step 9-14 a desired implant is selected. This selection will be based on factors such as the application, the size of bones involved, etc. Exemplary implants include a spacer/plug like those described above, a bone plate configured to receive or hold the carrier material, artificial discs, artificial joints, as well as any other desired types of implants. At step 9-16, the carrier material is reconstituted, using the adult stem cells isolated from the patent in step 9-12. The carrier material my be comprised of any desired type of carrier material such as, but not limited to, cancellous bone, cancellous chips, Hydroxylapatite, Helos, Tricalcium phosphate (bone ash), Collagen Sponge, etc. Once the carrier material is reconstituted, the carrier material is used with the implant (step 9-18). For example, in the example of the implant shown in FIG. 1, the carrier material (in that example, the plug 14) is used with the implant by inserting the carrier material into the spacer 12. With other implants, the carrier material may be used with the implant in other ways as well. At step 9-20, the implant is inserted at the fusion location. For example, in the in the example of the implant shown in FIG. 1, the implant is inserted between the vertebrae to be fused (FIG. 2, 7). In the example of a bone plate, that implant may be inserted over the bones to be fused together. In other examples, the implant is inserted in the proximity of the boney tissue to be fused.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A method of fusing adjacent vertebrae comprising:
providing a vertebral spacer having first and second opposing surfaces and an opening formed between the first and second opposing surfaces, and further comprising lateral scallops on opposite sides of the spacer and an opening on a front side of the vertebral spacer;
configuring a cancellous allograft plug to fit within the opening of the vertebral spacer and between the first and second opposing surfaces;
reconstituting the cancellous allograft plug using autologous stem cells by soaking the cancellous allograft plug in fluid containing the autologous stem cells, wherein the reconstituted cancellous allograft plug has a higher mass and volume after the reconstitution step than the cancellous allograft plug prior to the reconstitution step;
inserting the reconstituted cancellous allograft plug into the opening of the vertebral spacer between the first and second opposing surfaces; and
inserting the vertebral spacer and reconstituted cancellous allograft plug between the adjacent vertebrae to facilitate the fusion of the adjacent vertebrae, wherein the vertebral spacer containing the reconstituted cancellous allograft plug is inserted in a window cut into a side of a disc annulus, and wherein the window does not extend into end plates of the adjacent vertebrae.

2. The method of claim 1, further comprising forming a plurality of angled ridges in the first and second opposing surfaces of the pre-formed vertebral spacers to prevent migration of the selected pre-formed vertebral spacer.

3. The method of claim 1, wherein the collection of pre-formed vertebral spacers are made from a synthetic non-metallic radiolucent material.

4. The method of claim 3, wherein the synthetic non-metallic radiolucent material is comprised of a thermoplastic material.

5. The method of claim 3, wherein the synthetic non-metallic radiolucent material is comprised of Polyetheretherketones (PEEK).

6. The method of claim 3, further comprising forming a plurality of radio opaque markers in the synthetic non-metallic radiolucent material to allow a user to determine a position of the selected pre-formed vertebral spacer relative to a spine using x-rays.

7. A method of fusing adjacent vertebrae comprising:

isolating adult stem cells from a first person;

selecting a pre-formed vertebral spacer from a collection of pre-formed vertebral spacers having first and second opposing surfaces and an opening formed in the pre-formed vertebral spacer between the first and second opposing surfaces, and further comprising lateral scallops on opposite sides of the pre-formed vertebral spacer and an opening on a front side of the pre-formed spacer;

selecting a pre-formed cancellous allograft plug from a collection of pre-formed allograft plugs that corresponds to the selected pre-formed vertebral spacer to fit within the opening of the selected pre-formed vertebral spacer between the first and second opposing surfaces;

reconstituting the selected pre-formed cancellous allograft plug using the isolated adult stem cells from the first person to provide a reconstituted plug using the adult stem cells that will facilitate fusion of the adjacent vertebrae, wherein the selected pre-formed cancellous allograft plug has a higher mass and volume after the reconstitution step than the selected pre-formed cancellous allograft plug prior to the reconstitution step;

inserting the selected pre-formed cancellous allograft plug into the opening of the selected pre-formed vertebral spacer between the first and second opposing surfaces; and inserting the selected pre-formed vertebral spacer and the selected pre-formed cancellous allograft plug between the adjacent vertebrae of the first person to facilitate the fusion of the adjacent vertebrae, wherein the selected pre-formed vertebral spacer containing the selected pre-formed cancellous allograft plug is inserted in a window cut into a side of a disc annulus, and wherein the window does not extend into end plates of the adjacent vertebrae.

8. The method of claim 7, further comprising forming a plurality of angled ridges in the first and second opposing surfaces of the collection of pre-formed vertebral spacers to prevent migration of the selected pre-formed vertebral spacer when the selected pre-formed vertebral spacer is inserted between the adjacent vertebrae.

9. The method of claim 7, wherein the collection of pre-formed vertebral spacers are made from a synthetic non-metallic radiolucent material.

10. The method of claim 9, wherein the synthetic non-metallic radiolucent material is comprised of a thermoplastic material.

11. The method of claim 9, wherein the synthetic non-metallic radiolucent material is comprised of Polyetheretherketones (PEEK).

12. The method of claim 9, further comprising forming a plurality of radio opaque markers in the synthetic non-metallic radiolucent material to allow a user to determine a position of the selected pre-formed vertebral spacer relative to a spine using x-rays.

* * * * *